(12) United States Patent
Rashid

(10) Patent No.: US 10,835,413 B2
(45) Date of Patent: Nov. 17, 2020

(54) FLUENCY AID

(71) Applicant: Cirrus Logic International Semiconductor Ltd., Edinburgh (GB)

(72) Inventor: Tahir Rashid, Tewkesbury (GB)

(73) Assignee: Cirrus Logic, Inc., Austin, TX (US)

( * ) Notice: Subject to any disclaimer, the term of this patent is extended or adjusted under 35 U.S.C. 154(b) by 39 days.

(21) Appl. No.: 16/260,950

(22) Filed: Jan. 29, 2019

(65) Prior Publication Data

US 2019/0231585 A1 Aug. 1, 2019

Related U.S. Application Data

(60) Provisional application No. 62/624,428, filed on Jan. 31, 2018.

(30) Foreign Application Priority Data

Mar. 15, 2018 (GB) .................. 1804168.1

(51) Int. Cl.
*A61F 5/58* (2006.01)
*G10L 21/0208* (2013.01)
*G09B 19/04* (2006.01)
*G10L 21/003* (2013.01)
*G10L 21/057* (2013.01)

(52) U.S. Cl.
CPC ............... *A61F 5/58* (2013.01); *G09B 19/04* (2013.01); *G10L 21/003* (2013.01); *G10L 21/0208* (2013.01); *G10L 2021/0575* (2013.01)

(58) Field of Classification Search
CPC ..... A61F 5/58; G10L 21/0208; G10L 21/003; G10L 2021/0575; G09B 19/04
See application file for complete search history.

(56) References Cited

U.S. PATENT DOCUMENTS 5,794,203 A * 8/1998 Kehoe .................. A61F 5/58
704/271
2007/0049788 A1 * 3/2007 Kalinowski ............ A61F 5/58
600/23

FOREIGN PATENT DOCUMENTS

WO 2007024585 A2 3/2007

OTHER PUBLICATIONS

Combined Search and Examination Report under Sections 17 and 18(3), UKIPO, Application No. GB1804168.1, dated Sep. 18, 2018.

* cited by examiner

*Primary Examiner* — Yogeshkumar Patel
(74) *Attorney, Agent, or Firm* — Jackson Walker L.L.P.

(57) ABSTRACT

The present disclosure relates to a fluency aid comprising: a first microphone; a second microphone; and an altered auditory feedback, AAF, generator operable to receive a first input signal derived from sound detected by the first microphone and to generate a feedback signal for providing altered auditory feedback to a user of the fluency aid; wherein the fluency aid is configured such that a second input signal derived from sound detected by the second microphone bypasses the AAF generator.

16 Claims, 1 Drawing Sheet

FLUENCY AID

The present disclosure claims priority to U.S. Provisional Patent Application Ser. No. 62/624,428, filed Jan. 31, 2018, and United Kingdom Patent Application No. 1804168.1, filed Mar. 15, 2018, each of which is incorporated by reference herein in its entirety.

TECHNICAL FIELD

The present disclosure relates to a fluency aid, and in particular to a fluency aid for use by persons suffering from a stammer or other speech-related conditions to aid fluency of speaking.

BACKGROUND

Stammering affects about 1-3% of the world's population. From historical records available it is suggested that the condition has always affected 1-3% of the population and is agnostic of race, religion, wealth, and upbringing. Many with the condition are misjudged by the way they talk and as a result many are treated differently in society and may fail to fulfil their potential. The situation can be particularly difficult for children and young adults who may be bullied or ridiculed at school and may find themselves withdrawing from society at a time when they should be finding their place in the world. The condition leaves many feeling anxious and isolated.

There are a number of known auditory effects that can help alleviate stammering. Electronic devices have in the past been created to utilise these effects to help give stammerers greater fluency. Many of these devices are large and cumbersome and cannot be used without attracting further ridicule. More discrete devices still resemble medical devices and their cost puts them out of the reach of most stammerers.

Stammering and stuttering refer to the same condition, with the term stammer being used more in the UK and stutter being used more in the USA. The exact cause of stammering is unknown although it is now generally accepted that it is the result of the brain's neural circuits that control speech having been 'mis-wired'.

Altered auditory feedback as a therapy can be very effective with many people who suffer from a stammer. The present disclosure relates to a fluency aid, for people who stammer, that can differentiate between signals, related to speech, detected by different microphones, in order to provide altered auditory feedback to a user of the fluency aid.

STATEMENTS OF INVENTION

According to an example of a first aspect there is provided a fluency aid comprising: a first microphone; a second microphone; and an altered auditory feedback, AAF, generator operable to receive a first input signal derived from sound detected by the first microphone and to generate a feedback signal for providing altered auditory feedback to a user of the fluency aid; wherein the fluency aid is configured such that a second input signal derived from sound detected by the second microphone bypasses the AAF generator.

Altered Auditory Feedback is a technique for changing the information fed back to a person (for example a user of the fluency aid) in order to change or mask the person's perception of their own speech.

The fluency aid includes a first microphone and a second microphone. The first microphone is operable to detect sound from which a first input signal is derived. In an example, the sound detected by the first microphone may be a voice of a user. In another example the sound detected by the first microphone may be the voice of the user along with leakage from other sound sources. The first input signal may preferably be a signal derived from a sound corresponding to the user's voice. The AAF generator receives the first input signal and generates a feedback signal. The feedback signal may for example be generated from a first input signal to which one or more types of signal variation have been applied for the purpose of providing altered auditory feedback to the user. A second input signal derived from sound detected by the second microphone bypasses the AAF generator. In an example, sound detected by the second microphone is not received at the AAF generator and thus is not used in generation of the feedback signal. Altered auditory feedback may then be provided to a user of the fluency aid on the basis of the feedback signal. Therefore, according to an example, the feedback signal is generated on the basis of sound detected by the first microphone and not based on sound detected by the second microphone.

The fluency aid may preferably include more than one first and/or second microphone. In this case the AAF generator receives a first input signal derived from sound detected by the first microphones. The fluency aid is arranged such that a second input signal derived from sound detected by the second microphones bypasses the AAF generator. Multiple microphones may be positioned so as to detect the desired sound. For example, multiple first microphones may be positioned near the user to more clearly detect the user's voice, or may be directional microphones arranged so as to pick up the user's voice. In another example, multiple second microphones may be positioned to detect background noise around a user, which may include voices of other people near the user.

According to one or more examples, the feedback signal includes one or more of a masked auditory feedback, MAF, signal, a delayed auditory feedback, DAF, signal and a frequency altered feedback, FAF, signal.

Masked Auditory Feedback (MAF) refers to the use of sound to mask the speaker's own voice. In MAF a masking signal is applied to the input signal so as to be able to feedback to the user a predetermined amount of the input signal and a predetermined amount of the masking signal.

Delayed Auditory Feedback (DAF) refers to a technique whereby the speaker's voice is delayed before being presented to the speaker's ears. The level of improvement from stammering to fluency varies from user to user as does the long term effect. In cases where the user demonstrates a decreased effectiveness, altering the delay time has been reported to restore the effectiveness of DAF. The duration of the delay may for example lie in the range of 50-250 ms.

Frequency Altered Feedback (FAF) refers to a technique whereby the user's voice is shifted in frequency before being fed back to the user's ears. It is therefore also referred to as Frequency Shift Feedback (FSF). One approach is to shift the user's voice down one octave. The effectiveness of FAF on reducing stammering is similar to that of DAF. Some studies suggest FAF produces speech, closer to the user's normal speech, compared to MAF which tends to lead to louder speech and DAF which tends to lead to slower speech.

A combination of different forms of AAF provides an advantage of increased versatility and effectiveness to a broader range of stammerers and types of stammer.

Preferably, when the feedback signal includes a MAF signal, a masking sound is produced to mask sound detected by the first microphone.

A masking sound, which may for example be generated by a sound generator based on the masking signal, may take any suitable form, for example white noise, pink noise, tones or music. The form of the masking sound may be selected based on user preference, based on effectiveness at relieving the user from the symptoms of stammering or based on the situation, for example if the user needs to hear people that they are speaking to.

Preferably, in accordance with an example, the masking sound is faded out, when sound is no longer detected by the first microphone or in response to an operation of a switch.

In an example, the masking sound may be played (output) at an initial volume (loudness) which is reduced over time such that the masking sound becomes gradually quieter. This is advantageous to users who wish to hear the masking sound before beginning to speak, but who wish for the masking sound, and the masking effect, to be reduced over time. A user may therefore choose when to begin speaking based on a remaining volume of the masking sound. As the masking sound is faded, the masking effect becomes reduced. Therefore, a user may prefer to begin speaking when their own voice is only partially masked.

For some users, it may be preferable that the masking sound is played at a constant, initial volume, which is then gradually reduced once they have started speaking. Since some stammerers only stammer when starting to speak, once they have started speaking the masking sound may be reduced in volume so that they can hear their own voice again. This fading out of the masking sound, once the user begins speaking (once the voice detector detects a voice), allows the user to adjust the volume of their own voice, based on their own auditory feedback, so as to speak normally (at a normal volume).

A user may wish to control when the masking sound is stopped, rather than wait for it to fade out or otherwise. Therefore, a switch may be provided to initiate a fading out of the masking sound.

In another example, it may be preferable that the masking sound is played at a constant volume while the user is speaking. The masking sound is then gradually reduced once the user has stopped speaking (once sound is no longer detected by the first microphone).

Preferably, in accordance with one or more examples, the first microphone is positioned, in use, so as to be in a speech region in front of a user's mouth and/or the second microphone is positioned, in use, to detect background noise.

Positioning the first microphone in the speech region in front of a user's mouth provides the advantage that the first microphone may detect the user's voice clearly and as the dominant sound, meaning the feedback signal provided to the user is based mainly on the user's own speech. This reduces background noise leakage.

Preferably, the feedback signal is output at a loudness based on a loudness of sound detected by the first microphone.

In an example, sound detected by the first microphone forms the basis on which the feedback signal is generated. Therefore, outputting the feedback signal at a loudness (volume) based on the loudness of the sound detected by the first microphone allows the altered auditory feedback to be output at a loudness level comparable to, quieter than or louder than the loudness of the detected sound, as desired.

In an example, the sound detected by the first microphone is the user's voice. Therefore, it may be preferable to control that the feedback to the user is played back louder than the user's voice, for example, or quieter, depending on user preference or efficacy.

Preferably, the feedback signal is output at a loudness based on a loudness of the sound detected by the second microphone.

In an example, sound detected by the second microphone bypasses the AAF generator and is not sound on which the feedback signal is based. It may be desirable to output the feedback signal based on sound independent of the generation of the feedback signal.

In a further example, the sound detected by the second microphone is background noise. Therefore, it may be preferable to control that the feedback to the user is played back louder than the background noise, for example if the user does not wish to hear the background noise. Conversely, it may be preferable to play the feedback quieter than background noise, if for example the user is talking to other people whose voices are detected by the second microphone.

Preferably, the altered auditory feedback is output to both ears of the user.

Improved performance is achieved if the AAF is replayed into both ears. This then blocks or obscures background sounds or the speech of someone speaking to the user in a more predictable and controllable way.

Preferably, the AAF generator is activated or deactivated by a switch.

The switch may be any suitable switch for this purpose. The user may notice themselves starting to stammer or may wish to speak without the AAF. Therefore a switch may be provided to activate and/or deactivate the AAF generator. The switch may for example have an ON state and an OFF state, wherein, based on the switch states, the AAF generator is switched on or off, respectively.

Preferably, the feedback signal, for providing altered auditory feedback to the user, is changed by applying one or more variations, based on a predefined set of variations. The variations may for example be applied automatically by the AAF generator.

In an example, a property of the feedback signal is changed based on one or more methods of AAF. A user's brain can often quickly adapt to the "trick" being played on it, i.e. the effectiveness of the techniques used to increase fluency can be diminished over time. Therefore, it can be beneficial to combine multiple techniques to keep the brain from adapting and to further prolong the user's fluency. In an example, multiple techniques may be automatically applied at random so that the user's brain cannot adapt.

As mentioned above, Altered Auditory Feedback (AAF) may include for example: Delayed Auditory Feedback (DAF); and Frequency Altered Feedback (FAF). An example of a change in the type of variation may therefore be to change between DAF and FAF. An example of a change in a parameter of the variation may for example be to change a delay time in DAF or change a frequency shift in FAF.

Preferably, the feedback signal is changed by applying different variations at random or based on an amount of time having elapsed.

Triggering the variation to be applied at random is advantageous in that the user's brain is less likely to adapt, or learn, to compensate for the AAF or any specific pattern of the change. Some users may achieve equal success by changing the property of the variation based on a timer.

According to one or more examples, the fluency aid may further comprise a pacing signal generator to output an audible sound, at regularly timed intervals. Preferably, the audible sound is a click or tone sound.

Speaking to a timed rhythm is another method of improving fluency in stammerers. There are many different approaches to speech therapy and if the stammerer shows a reduction in stammering when speaking to a timed rhythm then this can be a valuable tool and may be used in combination with other forms of therapy. Users of the fluency aid may prefer specific sounds to which to time their speech. A click or tone provides a clear regular beat, easily recognisable among other sounds.

Preferably, the audible sound is faded out over time following detection of sound, detected by the first microphone.

In an example, the user is given a regularly output audible sound to get them started, wherein the audible sound is faded out once the user gets going. The user may prefer the audible sound to continue being output at regularly timed intervals even when the user is speaking. Alternatively, a user may prefer that the audible sound continues, but is faded either completely or partially, to allow the user to hear themselves speak over the audible sound. Further still, some users may only require the regularly timed audible sound to help them start speaking and therefore the audible sound may be stopped following detection of sound by the first microphone.

Preferably, the first microphone has a first gain and the second microphone has a second gain, different to the first gain.

In an example a fluency aid may comprise a voice detector having a first gain and positioned to detect a voice of a user; a background noise detector having a second gain, different to the first gain, and positioned to detect background noise around the user as a background noise signal; and a feedback generator to generate altered auditory feedback, AAF, based on the voice of the user, wherein the AAF and the background noise are output to the user.

In accordance with an example, the voice detector may be a first microphone as described above. The background noise detector may be a second microphone. Preferably, the gain of the first microphone may be higher than that of the second microphone. Alternatively, the gain of the first microphone may be lower than that of the second microphone.

According to an example of a second aspect there is provided a fluency aid comprising: a first microphone; a second microphone; and an altered auditory feedback, AAF, generator operable to receive an input signal derived from sound detected by the first microphone and to generate a feedback signal for providing altered auditory feedback to a user of the fluency aid; wherein the AAF generator does not receive an input signal derived from sound detected by the second microphone.

According to an example of a further aspect there is provided a telephone, headphones, acoustic noise cancelling headphones, smart watch, or other portable device comprising the fluency aid as described above. These and any other wearable devices may include a fluency aid as described above.

BRIEF DESCRIPTION OF DRAWINGS

For a better understanding of the present disclosure, and to show how the same may be carried into effect, reference will now be made, by way of example only, to the accompanying drawings in which.

Throughout this description any features which are similar to features in other figures have been given the same reference numerals.

DETAILED DESCRIPTION

The description below sets forth example fluency aids according to this disclosure. Further examples and implementations will be apparent to those having ordinary skill in the art. Further, those having ordinary skill in the art will recognize that various equivalent techniques may be applied in lieu of, or in conjunction with, the examples discussed below, and all such equivalents should be deemed as being encompassed by the present disclosure.

The arrangements described herein can be implemented in a wide range of devices and systems. However, for ease of explanation, an illustrative example will be described.

Figure 1:
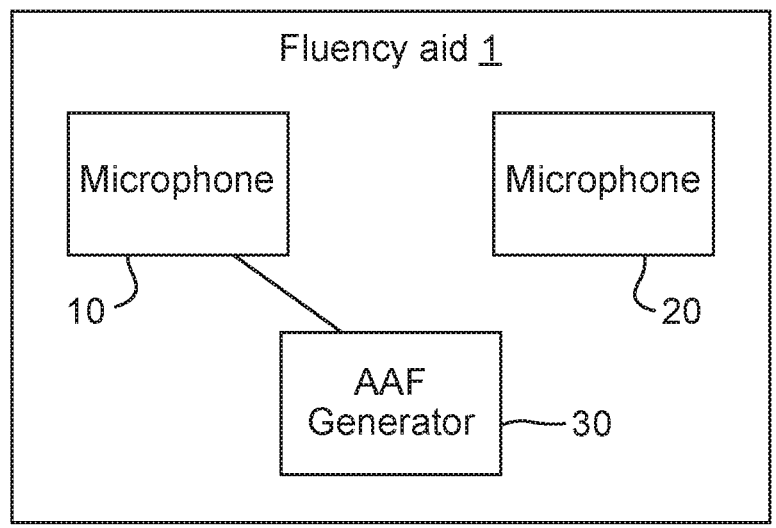
FIG. 1 is an example of a fluency aid according to the present disclosure.

FIG. 1 illustrates an example of a fluency aid 1 according to the present disclosure. As shown, a fluency aid 1 includes a first microphone 10, a second microphone 20 and an altered auditory feedback, AAF, generator 30.

According to the illustrated example the AAF generator 30 is operable to receive a first input signal derived from sound detected by the first microphone 10 and to generate a feedback signal for providing altered auditory feedback to a user of the fluency aid. The fluency aid is configured such that a second input signal derived from sound detected by the second microphone 20 bypasses the AAF generator 30.

In an example, the sound detected by the first microphone may be a voice of a user or the voice of the user along with leakage from other sound sources. The first input signal may preferably be a signal derived from a sound corresponding to the user's voice. The AAF generator receives the first input signal and generates a feedback signal. The feedback signal may for example be generated from a first input signal to which one or more types of signal variation have been applied for the purpose of providing altered auditory feedback to the user. Altered auditory feedback may then be provided to a user of the fluency aid on the basis of the feedback signal. In an example, sound detected by the second microphone is not received at the AAF generator and thus is not used in generation of the feedback signal. Therefore, according to an example, the feedback signal is generated on the basis of sound detected by the first microphone and not based on sound detected by the second microphone. This provides the advantage that the feedback to the user is more controllable and may be based on a desired sound with other sounds excluded from the AAF.

In an example, the feedback signal may include one or more of a masked auditory feedback, MAF, signal, a delayed auditory feedback, DAF, signal and a frequency altered feedback, FAF, signal. In accordance with the example, when the feedback signal includes a MAF signal, a masking sound is produced to mask sound detected by the first microphone.

In a further example, the first microphone is positioned, in use, so as to be in a speech region in front of a user's mouth and/or the second microphone is positioned, in use, to detect background noise. Preferably, in accordance with an example the feedback is output at a loudness based on a loudness of sound detected by the first microphone or that detected by the second microphone. At output, the feedback signal may correspond to a feedback sound, wherein the feedback sound resembles the user's voice with one or more types of AAF applied thereto.

Figure 2:
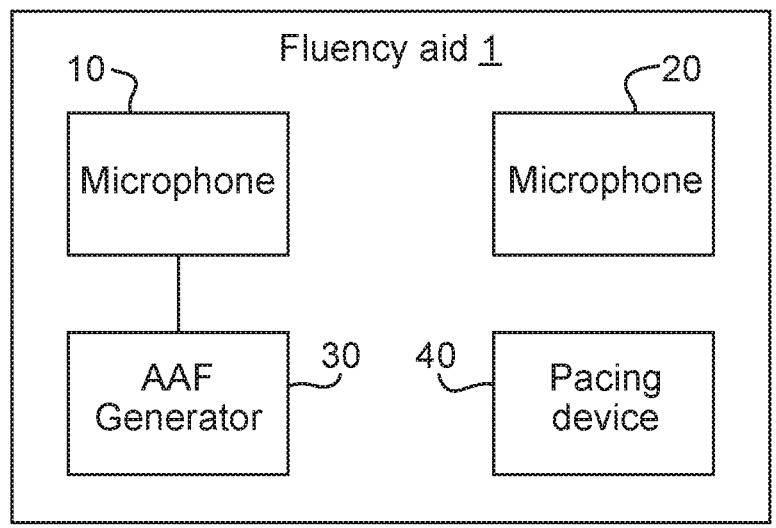
FIG. 2 is an example of a fluency aid according to the present disclosure further comprising a pacing device.

FIG. 2 illustrates a further example of a fluency aid 1 according to the present disclosure, wherein the fluency aid 1 further includes a pacing device 40 to output an audible sound to the user at regularly timed intervals. In an example the audible sound is faded out following detection of sound, detected by the first microphone.

According to one or more examples, a user of the fluency aid may prefer a specific sound, as the audible sound, to which to time their speech. A click or tone may provide a clear regular beat, easily recognisable among other sounds. The regular timing of the output of the audible sound may be programmable based on a timing which aids the user's fluency.

In accordance with an example, a user may be given a regularly output audible sound to get them started with speaking, wherein the audible sound is faded out once the user gets going. The user may prefer the audible sound to continue being output at regularly timed intervals even when the user is speaking. Alternatively, a user may prefer that the audible sound continues, but is faded either completely or partially, to allow the user to hear themselves speak over the audible sound. Further still, some users may only require the regularly timed audible sound to help them start speaking and therefore the audible sound may be stopped completely following detection of sound by the first microphone.

In an example, the fluency aid 1, including the pacing device 40, may be used by a stammerer who has found that speaking in time with a regular beat aids fluency of speech. The pacing device 40 is operable to output the regular beat, which is an example of an audible sound, as described above. The pacing device 40 may be activated and deactivated by the switch in a similar manner to the AAF generator 30.

Any of the above-described examples may be included in a telephone, headphones, acoustic noise cancelling headphones, smart watch, or other portable or wearable device.

It will be appreciated that features of any of the above aspects and examples may be provided in any combination with the features of any other of the above aspects and examples.

The fluency aid may be at least partly implemented within a speaker housing. The housing may be, e.g. that of a wired or wireless headset, an ear-bud a supra-aural head phone or a speaker portion of a mobile device such as a mobile phone handset. Alternatively, the parts associated with one or more features of the fluency aid may be provided in an apparatus separate to the apparatus that comprises the at least one speaker. For example, the fluency aid may be at least partly implemented within a mobile handset or a "dongle", wherein a wired or wireless connection is provided between the apparatuses. According to one implementation the switch and/or the voice detector are provided in an apparatus that is separate from the apparatus, e.g. headset or ear-bud.

It should be noted that the above-mentioned examples illustrate rather than limit the disclosure, and that those skilled in the art will be able to design many alternative configurations without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope. The features of any dependent claim may be combined with the features of any of the independent claims or other dependent claims.

The invention claimed is:

1. A fluency aid comprising:
   a first microphone;
   a second microphone; and
   an altered auditory feedback, AAF, generator operable to receive a first input signal derived from sound detected by the first microphone and to generate a feedback signal for providing altered auditory feedback to a user of the fluency aid;
   wherein the fluency aid is configured such that a second input signal derived from sound detected by the second microphone bypasses the AAF generator; and
   wherein the first microphone is positioned, in use, so as to be in a speech region in front of a user's mouth and/or the second microphone is positioned, in use, to detect background noise.

2. The fluency aid according to claim 1, wherein the feedback signal includes one or more of a masked auditory feedback, MAF, signal, a delayed auditory feedback, DAF, signal and a frequency altered feedback, FAF, signal.

3. The fluency aid according to claim 2, wherein, when the feedback signal includes a MAF signal, a masking sound is produced to mask sound detected by the first microphone.

4. The fluency aid according to claim 3, wherein the masking sound is faded out, when sound is no longer detected by the first microphone or in response to an operation of a switch.

5. The fluency aid according to claim 1, wherein the feedback signal is output at a loudness based on a loudness of sound detected by the first microphone.

6. The fluency aid according to claim 1, wherein the feedback signal is output at a loudness based on a loudness of the sound detected by the second microphone.

7. The fluency aid according to claim 1, wherein the altered auditory feedback is output to both ears of the user.

8. The fluency aid according to claim 1, wherein the AAF generator is activated or deactivated by a switch.

9. The fluency aid according to claim 1, wherein the feedback signal, for providing altered auditory feedback to the user, is changed by applying one or more variations, based on a predefined set of variations.

10. The fluency aid according to claim 9, wherein the feedback signal is changed by applying different variations at random or based on an amount of time having elapsed.

11. The fluency aid according to claim 1, further comprising:
    a pacing signal generator to output an audible sound at regularly timed intervals.

12. The fluency aid according to claim 11, wherein the audible sound is faded out following detection of sound, detected by the first microphone.

13. The fluency aid according to claim 1, wherein the first microphone has a first gain and the second microphone has a second gain, different to the first gain.

14. A fluency aid comprising:
    a first microphone to detect a voice of a user;
    a second microphone to detect background noise; and
    an altered auditory feedback, AAF, generator operable to receive an input signal derived from sound detected by the first microphone and to generate a feedback signal for providing altered auditory feedback to a user of the fluency aid;

wherein the AAF generator does not receive an input signal derived from sound detected by the second microphone.

15. A telephone, headphones, acoustic noise cancelling headphones, smart watch, or other portable device comprising the fluency aid according to claim 1.

16. A telephone, headphones, acoustic noise cancelling headphones, smart watch, or other portable device comprising the fluency aid according to claim 14.

* * * * *